US012582656B2

(12) United States Patent
Papasotiriou

(10) Patent No.: US 12,582,656 B2
(45) Date of Patent: Mar. 24, 2026

(54) NUCLEOTIDE ANALOGUES

(71) Applicant: R.G.C.C. Holdings AG, Zug (CH)

(72) Inventor: Ioannis Papasotiriou, Oberägeri (CH)

(73) Assignee: R.G.C.C. Holdings AG, Zug (CH)

( * ) Notice: Subject to any disclaimer, the term of this patent is extended or adjusted under 35 U.S.C. 154(b) by 719 days.

(21) Appl. No.: 17/914,634

(22) PCT Filed: Mar. 23, 2021

(86) PCT No.: PCT/EP2021/057490
§ 371 (c)(1),
(2) Date: Sep. 26, 2022

(87) PCT Pub. No.: WO2021/191236
PCT Pub. Date: Sep. 30, 2021

(65) Prior Publication Data
US 2023/0118992 A1 Apr. 20, 2023

(30) Foreign Application Priority Data
Mar. 27, 2020 (EP) .................................... 20166373

(51) Int. Cl.
*A61K 31/517* (2006.01)
*A61P 11/00* (2006.01)
*A61P 31/14* (2006.01)

(52) U.S. Cl.
CPC ............ *A61K 31/517* (2013.01); *A61P 11/00* (2018.01); *A61P 31/14* (2018.01)

(58) Field of Classification Search
CPC ......... A61K 31/517; A61P 31/14; A61P 11/00
See application file for complete search history.

(56) References Cited

FOREIGN PATENT DOCUMENTS

| | | | | |
|---|---|---|---|---|
| JP | 2020-524703 A | 8/2020 | | |
| WO | 2010/026029 A1 | 3/2010 | | |
| WO | 2015/200219 A1 | 12/2015 | | |
| WO | WO2018/237084 A1 * | 12/2018 | .......... | C07D 495/04 |

OTHER PUBLICATIONS

Zhang et al. Journal of Virology, Jun. 2010, p. 6050-6059. (Year: 2010).*
Ioanna Vlachou et al., "9-(4-Methoxyquinazolin-2-yl)-9H-purin-6-a mine", Molbank, 2016, p. M885, 3 pages, vol. 2016, No. 1.
C.O. Usifoh et al., "Triflate-mediated Synthesis of 3-(4-Methoxyquinazolin-2-yl)-quinazolin-2,4-(1H,3H)-dione and its Antimicrobial Activity", Scientia Pharmaceutica, 2002, pp. 123-128, vol. 70, No. 2.
Dorota G. Piotrowska et al., "New Isoxazolidine-Conjugates of Quinazolinones-Synthesis, Antiviral and Cytostatic Activity", Molecules Online, 2016, p. 959, 15 pages, vol. 21, No. 7.
Lee Jun Young et al., "Design, synthesis and biological evaluation of 2-aminoquinazolin-4(3H)-one derivatives as potential SARS-CoV-2 and MERS-CoV treatments", Bioorganic & Medicinal Chemistry Letters, 2021, p. 127885, 4 pages, vol. 39.
Ioanna Vlachou et al., "9-(4-Methoxyquinazolin-2-yl)-9H-purin-6-amine", Molbank, 2016, p. M885, 3 pages.
International Search Report of PCT/EP2021/057490 dated Jun. 4, 2021 [PCT/ISA/210].
Written Opinion of PCT/EP2021/057490 dated Jun. 4, 2021 [PCT/ISA/237].
"Registry Copyright 2024 ACS on STN", CAS No. 1090417-27-8, 1258734-77-8, 1427945-70-7, and 1797105-51-1 , searched Aug. 22, 2024, 8 pages.

* cited by examiner

*Primary Examiner* — Scarlett Y Goon
*Assistant Examiner* — Samantha Lynn Schachermeyer
(74) *Attorney, Agent, or Firm* — Sughrue Mion, PLLC

(57) ABSTRACT

A compound according to the formula I

I

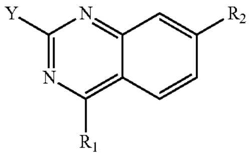

for use in the treatment of coronavirus infection and/or a respiratory disease caused by a coronavirus, wherein $R_1$ is chosen from alkoxy groups such as for example methoxy or ethoxy, hydroxyl group, and phosphate group,
wherein $R_2$ is a group chosen from halogen and/or hydrogen,
wherein Y is a nucleic base, preferably a purine or pyrimidine.

6 Claims, 2 Drawing Sheets

NUCLEOTIDE ANALOGUES

CROSS REFERENCE TO RELATED APPLICATIONS

This application is a National Stage of International Application No. PCT/EP2021/057490 filed on Mar. 23, 2021, claiming priority based on European Patent Application No. 20166373.9 filed on Mar. 27, 2020.

TECHNICAL FIELD

The present invention relates to nucleotide analogues, in particular in the treatment of viral infections such as infections by MERS-CoV, SARs-CoV or SARS-CoV-2.

PRIOR ART

Conjugate compounds consisting of quinazoline and adenine moieties have been synthesized as a precursor of a potential biologically active target compound. The structure of 9-(4-methoxyquinazolin-2-yl)-9H-purin-6-amine (2) was characterized and reported in 9-(4-Methoxyquinazolin-2-yl)-9H-purin-6-amine; I. Vlachou, E. Kourtidou and I. Papasotiriou; Molbank 2016, 2016(1), M885; https://doi.org/10.3390/M885.

Coronaviruses are a group of enveloped positive-sense RNA viruses. Their genome size is about 30 kilobases in length, which is unusually large for RNA viruses. Other common features of this subfamily include a large replicase gene, which encodes several enzymatic activities and a unique replication strategy.

They typical organization of the coronavirus genome is 5'-leader-UTR-replicase—S (Spike)—E (Envelope)—M (Membrane)—N (Nucleocapsid)-3'UTR. The genome also contains a 5' methylated cap and a 3' polyadenylated tail that enables it to act as an mRNA for translation. A notorious coronavirus, namely SARS-CoV-2, is a positive-sense single-stranded RNA virus that is highly contagious in humans and is the cause of the ongoing pandemic of coronavirus disease 2019 (COVID-19) that has been designated a Public Health Emergency of International Concern by the World Health Organization (WHO).

Infection begins when the virion attaches to the host cell. This is initiated by interactions between the viral spike (S) glycoprotein and the host cell ACE2 receptor. Following attachment, the virus must next release its genome into the host cell cytosol. This is accomplished by priming of the spike glycoprotein by the serine protease TMPRSS2, which entails S protein cleavage. This ultimately allows fusion of the viral and cellular membranes and entry of the virus to the host cell. The next step in the coronavirus life cycle is the translation of the replicase gene using the cell's machinery. The replicase gene is about 20 kilobases in length and encodes two ORFS, orf1a and orf1ab, which express the pp1a and pp1ab polyproteins, respectively. Each polyprotein contains several nsps (non-structural proteins) that display various enzymatic activities. Each polyprotein is cleaved by the virus's own proteases into the individual nsps. The main protease of coronaviruses is a serine type protease, Mpro. The first high-resolution crystal structure of COVID-19 coronavirus 3CL hydrolase (Mpro) has been determined by Zihe Rao and Haitao Yang's research team at ShanghaiTech University (PDB entry 6LU7).

Next, many of the nsps assemble into the replicase-transcriptase complex (RTC) which is responsible for RNA replication and transcription of the sub-genomic RNAs. The nsps that comprise the complex include:

- the RNA-dependent RNA polymerase (nsp12) that mediates synthesis of genomic RNA
- the 3'-to-5' exonuclease (nsp14) that is involved in proofreading and N7-methyltransferase activity The translation and assembly of the RTC complex is followed by viral RNA synthesis which produces both genomic and sub-genomic RNAs. During replication, full-length negative-sense RNA copies of the genome are produced by RNA-dependent RNA polymerase and used as templates for full-length positive-sense RNA genomes. During transcription, a subset of sub-genomic RNAs, is produced through discontinuous transcription.

In an effort to stop the spread and provide effective therapeutic options to patients affected by SARS-Cov-2, there exists a need to provide new compounds that can be used to treat patients infected by SARS-CoV-2 by disrupting viral replication by targeting the essential enzyme of RNA-dependent RNA polymerase.

SUMMARY OF THE INVENTION

The present invention provides nucleotide analogues which can be used in the treatment of disease or a respiratory disease caused by MERS-CoV, SARS-CoV-2 or SARS-CoV.

It is thus an object of the present invention to provide a compound according to the formula I

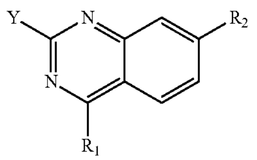

I for use in the treatment of coronavirus infection and/or a respiratory disease caused by a coronavirus, wherein $R_1$ is a group chosen from alkoxy groups such as for example methoxy or ethoxy, hydroxyl group, phosphate group, wherein $R_2$ is a group chosen from halogen and/or hydrogen, wherein Y is a nucleic base, preferably a purine or pyrimidine.

Said compounds may thus be used as inhibitors of the RNA-dependent RNA polymerase of MERS-CoV, SARS-CoV-2 or SARS-CoV either in vivo or in vitro.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
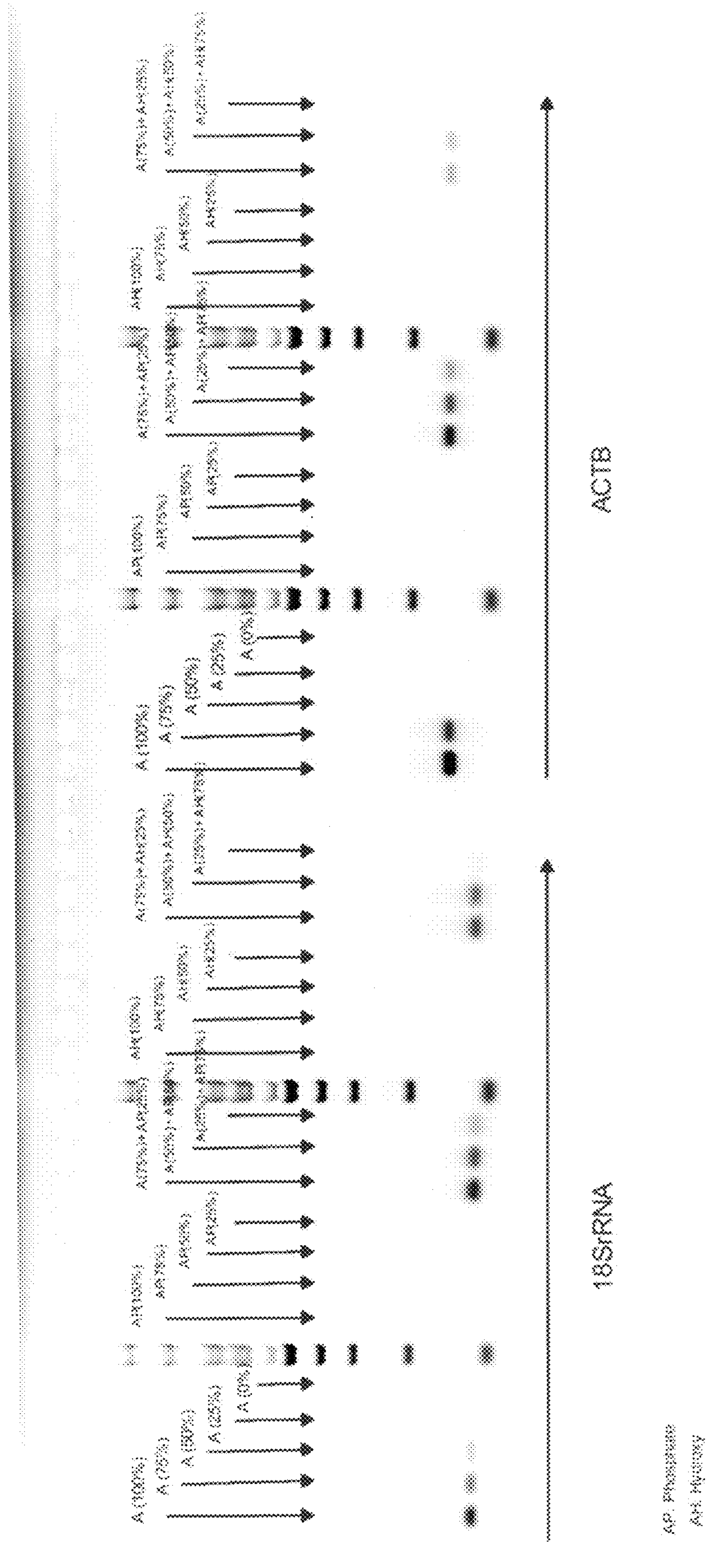
FIG. 1 shows a photograph of an agarose gel where PCR amplification products are visible as bands for varying concentrations of the compounds according to the invention together with conventional dNTPs.

The RNA-dependent RNA polymerase (nsp12) is directly involved in the replication and transcription of the viral genomic RNA. Studies have shown that nsp12 possesses some activity on its own but the addition of the nsp7 and nsp8 co-factors results in significant increase of polymerase activity. It is highly likely that additional nsp subunits are also needed to carry out the full repertoire of viral replication. However, the nsp12-nsp7-nsp8 complex so far represents the minimal complex required for nucleotide polymerization. Sequence analysis across the coronavirus subfamily members reveals that the template entry, template-primer exit, the NTP tunnels and the polymerase-active site are the most highly conserved surfaces on nsp12. In addition, there are seven motif regions (A-G), involved in template and nucleotide binding, which were also found to be conserved among the coronavirus subfamily.

The polymerase active site is composed of motifs A and C and supported by motifs B and D. The RNA template passes by motif G before entering the active site while incoming NTPs enter through a tunnel and interact with motif F. Once in the active site, NTPs are likely to form hydrogen bonds with T680, N691 and D623. All three of these residues are conserved across the coronavirus family.

In SARS-CoV-2, nsp12 is 932 amino acids in length and covers positions 4395 to 5324 of pp1ab (UniProtKB id: P0C6X7). There is no experimental structure of the protein available as of the date of filing. BLASTing the protein sequence against the PDB revealed that the closest homolog of the protein is nsp12 of SARS-CoV. The two proteins share a 96.35% sequence identity which covers 99% of SARS-CoV-2 nsp12. The SARS-CoV nsp12 structure is deposited in PDB entry 6NUR.

We created a homology model with the SWISS-MODEL webserver as well as ICM Pro using the 6NUR 3D structure as the template. Both are good quality models and after superposition they achieved a TM-Score of 0.99210. The RMSD between the two models is 1.14 and mostly stems from the insertion of a gap at a different position between the two softwares. As a result, the loop in this region obtains a different conformation in each model. The SWISS-MODEL-derived homology model was used as the structure upon which the docking of the inventive compounds was performed.

Based on the above-mentioned homology modelling, it is expected that the nucleotide analogues of the present invention will be incorporated to a newly synthesized RNA chain and cause a premature termination of replication in vitro and in vivo.

The present invention provides compounds according to the formula I

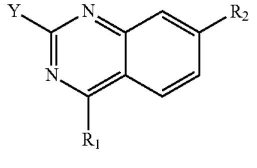

I for use in the treatment of coronavirus infection and/or a respiratory disease caused by a coronavirus, wherein $R_1$ is a group chosen from alkoxy groups such as for example methoxy or ethoxy, hydroxyl group, phosphate group, wherein $R_2$ is a group chosen from halogen and/or hydrogen, wherein Y is a nucleic base, preferably a purine or pyrimidine.

In the case where the nucleic base is a purine, the purine is linked to the quinazoline moiety via its 9-position.

In the case where the nucleic base is a pyrimidine, the purine is linked to the quinazoline moiety via its 1-position.

The compounds according to the formula I are conjugates of a nucleic bases such as nucleic bases found in the genetic code of organisms or viruses with a quinazoline moiety modified at its 4-position.

The compounds according to the formula I are conjugates of a nucleic bases such as nucleic bases found in the genetic code of organisms or viruses with a quinazoline moiety further modified at its 7-position with a halogen or a halogenated residue such as for example fluorine.

The nucleic bases may be canonical nucleic bases such as adenine (A), cytosine (C), guanine (G), thymine (T), and uracil (U). However, the nucleic bases useful in the compounds according to the present invention may further be modified nucleic bases or artificial nucleic bases such as for example xanthine, hypoxanthine, 7-methylguanine, $N^2$-acetylguanine, $N^4$-acetylcytosine, or isoguanine.

In a preferred embodiment, in the compounds according to the formula I, $R_1$ is a group is preferably chosen from hydroxyl group or phosphate group, most preferably is a phosphate group.

In a preferred embodiment, in the compounds according to the formula I, Y is a purine such as adenine or guanine, most preferably is adenine.

In a preferred embodiment, in the compounds according to the formula I, Y is a pyrimidine such as cytosine, thymine, or uracil. Further, in the compounds according to the formula I, Y may also be a pyrimidine analogue such as 5-fluorocytosine.

In a preferred embodiment, in the compounds according to the formula I, Y is cytosine, $R_1$ is hydroxyl and $R_2$ is hydrogen:

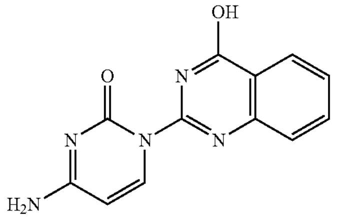 [SMILES: Nc1ccn(-c2nc(O)c3ccccc3n2)c(=O)n1]

In a preferred embodiment, in the compounds according to the formula I, Y is 5-fluorocytosine, $R_1$ is hydroxyl and $R_2$ is hydrogen:

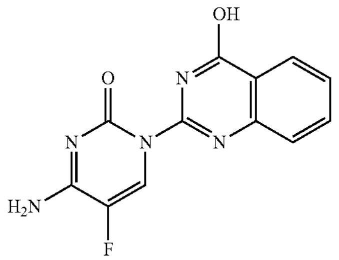 [SMILES: Nc1nc(=O)n(-c2nc(O)c3ccccc3n2)cc1F]

In a preferred embodiment, in the compounds according to the formula I are preferably for use in the treatment of coronavirus infection and/or a disease or respiratory disease caused by a MERS-CoV, SARS-CoV or SARS-CoV-2. In a preferred embodiment, the disease caused by SARS-CoV-2 is COVID-19.

In a preferred embodiment, the compound according to the formula I is 2-(6-amino-9H-purin-9-yl)quinazolin-4-ol.

In a preferred embodiment, the compound according to the formula I is 2-(6-amino-9H-purin-9-yl)quinazolin-4-yl dihydrogen phosphate.

In a preferred embodiment, the compound according to the formula I is 2-(6-amino-9H-purin-9-yl)-7-fluoro-quinazolin-4-ol.

In a preferred embodiment, when in the compound according to the formula I Y is guanine or N-acetylguanine, and $R_1$ is hydroxyl, the quinazoline moiety may further be modified at its 7-position with a halogen or a halogenated residue:

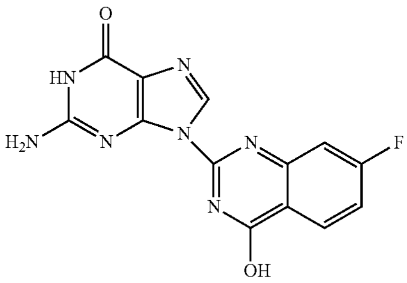 [SMILES: Nc1nc2c(ncn2-c2nc(O)c3ccc(F)cc3n2)c(=O)[nH]1]

In a preferred embodiment, the compound according to the formula I is 2-(6-amino-9H-purin-9-yl)-7-fluoro-quinazolin-4-yl dihydrogen phosphate.

In a preferred embodiment, in the compound according to the formula I, Y is N-acetylguanine, and $R_1$ is hydroxyl, the quinazoline moiety may or may not be modified at its 7-position with a halogen or a halogenated residue:

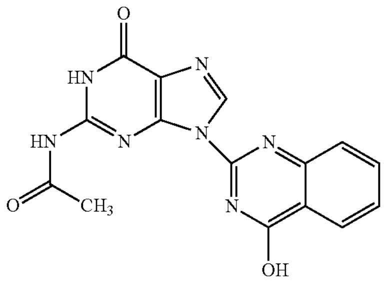 [SMILES: CC(=O)Nc1nc2c(ncn2-c2nc(O)c3ccccc3n2)c(=O)[nH]1]

In a preferred embodiment, in the compound according to the formula I, Y is $N^4$-acetylcytosine, and $R_1$ is hydroxyl, the quinazoline moiety may or may not be modified at its 7-position with a halogen or a halogenated residue:

The present invention further provides for a pharmaceutical formulation comprising at least one of a compound according to the formula I for use in the treatment of coronavirus infection and/or a respiratory disease caused by a coronavirus such as MERS-CoV, SARS-CoV-2 or SARS-CoV, wherein R may be a group chosen from alkoxy groups such as for example methoxy or ethoxy, hydroxyl group, phosphate group and where preferably said pharmaceutical formulation comprises 2-(6-amino-9H-purin-9-yl)quinazolin-4-ol or 2-(6-amino-9H-purin-9-yl)quinazolin-4-yl dihydrogen phosphate, or both.

The present invention even further provides a compound as above according to the formula I for inhibiting a coronavirus RNA-dependent RNA polymerase, in particular MERS-CoV, SARS-CoV-2 or SARS-CoV RNA-dependent RNA polymerase, more in particular NSP12 of SARS-CoV2, wherein R may be a group chosen from alkoxy groups such as for example methoxy or ethoxy, hydroxyl group, phosphate group and where preferably the compound according to the formula I is 2-(6-amino-9H-purin-9-yl)quinazolin-4-ol or 2-(6-amino-9H-purin-9-yl)quinazolin-4-yl dihydrogen phosphate.

In a preferred embodiment, the pharmaceutical formulation is an oral formulation such as a tablet or capsule or a formulation for injection.

EXPERIMENTAL DATA

Synthesis of Nucleotide Analogues

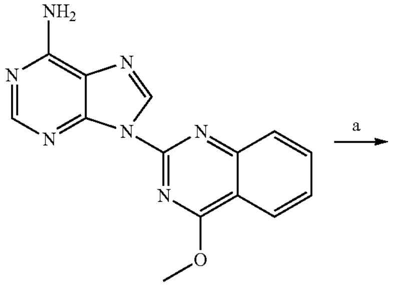

9-(4-methoxyquinazolin-2-yl)-9H-purin-6-amine

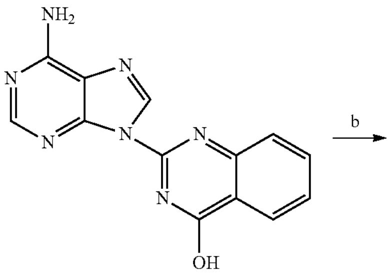

2-(6-amino-9H-purin-9-yl)quinazolin-4-ol

-continued

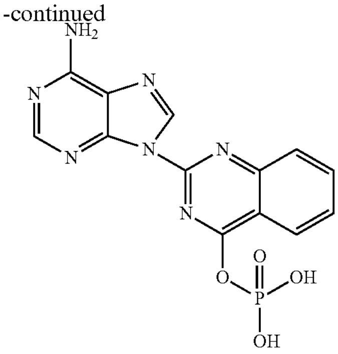

2-(6-amino-9H-purin-9-yl)quinazolin-4-yl dihydrogen phosphate a: 1-Dodecanthiol, $Cs_2CO_3$, DMSO b: $P_2O_5$, TBAB, $H_2O_2$ 30%, $CH_3CN/H_2O$ (1/1)

To a clean dry round-bottom flask, which was purged with nitrogen to remove water traces and other particles, 9-(4-methoxyquinazolin-2-yl)-9H-purin-6-amine (0.7922 g, 2.7 mmol) and 2.7 ml of DMSO were added. Then cesium carbonate (2.6063 g, 8.0 mmol) were added and finally 1-docecanthiol (0.99 ml, 4.0 mmol). The solution was stirred at room temperature for 1 h. The reaction mixture poured into crushed ice and filtered. The solid was purified with flash chromatography to get the desired product in 20% yield.

To a cooled solution (0° C.) of phosphorus pentoxide (0.0694 g, 0.5 mmol) in 24 ml $CH_3CN/H_2O$ (1/1), a 30% solution of hydrogen peroxide (1.8 ml) was added dropwise and was stirred for 5 min. Then tetra-n-butylammonium bromide (0.97 g, 3 mmol) and 2-(6-amino-9H-purin-9-yl) quinazolin-4-ol (0.279 g, 1 mmol), were added and stirred for 5 h at 0° C. The reaction mixture was filtered and then the solid was diluted in 20 ml of MeOH 3 times to get 2-(6-amino-9H-purin-9-yl)quinazolin-4-yl dihydrogen phosphate in 49% yield.

To a clean dry round-bottom flask, which was purged with nitrogen to remove water traces and other particles, a well-grounded mixture of adenine (1.3512 g, 10 mmol), 2-chloro hydroxyquinazoline (2.34 g, 13 mmol), cesium carbonate (3.2612 g, 10 mmol) and silica gel (3.5 g) was added under inert atmosphere. Then 20 mL of dry DMSO was added. The solution was stirred at 130° C. for 3.5 h and then it was poured into ice cold water and filtered.

Influence of Polymerase

The two substances which were tested are 2-(6-amino-9H-purin-9-yl)quinazolin-4-ol (Hydroxy substance) and 2-(6-amino-9H-purin-9-yl)quinazolin-4-yl dihydrogen phosphate (Phosphate substance).

On the first set of experiments the ability of two substances to block the polymerization it was tested, since they are modified nucleotide analogs. Endpoint PCR reactions were performed using a commercial template and two housekeeping genes (18SrRNA and Actin). The reaction took place using different concentrations of conventional dNTPs (dATP, dCTP, dGTP and dTTP), as well as different concentrations of our products and combination of them. The PCR products were then analyzed with gel electrophoresis (3%). The concept is that the use of modified nucleotide analogs, can inhibit the polymerization, since the 3'-5' phosphodiester bonds cannot be formed. Furthermore, the mix of conventional dATP and modified adenosine analogs should create both the final product as well as smaller fragments, which will be observed as "smear" on the agarose gel. The data are presented in the image below and in FIG. 1.

Based on the above data it can be demonstrated that the addition of modified nucleotide analogues according to the present invention inhibits the reactions, since no products are observed. On the other hand, the mix of conventional/modified adenosine nucleotide result in the presentation of both the final product, and a smear, as it was expected.

Each reaction contains 10 mM of each dATP, dCTP, dGTP and dTTP. In 75% dATP, we used 7.5 mM dATP and 10 mM of the rest. In 50% dATP, we used 5.0 mM dATP and 10 mM of the rest (dCTP, dGTP, dTP). In 25% dATP, we used 2.5 mM dATP and 10 mM of the rest (dCTP, dGTP, dTP). In 75% A: 25% AP (or AH) we, we used 7.5 mM of conventional dATP, 2.5 of the modified adenine analogue and 10 mM of the rest (dCTP, dGTP, dTP). In 50% A: 50% AP (or AH) we used 5.0 mM of conventional dATP, 5.0 mM of the respective modified adenine analogue and 10 mM of the rest (dCTP, dGTP, dTP). In 25% A: 75% AP (or AH) we used 2.5 mM of conventional dATP, 7.5 mM of the respective modified adenine analogue and 10 mM of the rest (dCTP, dGTP, dTP). All the concentrations are referred to the initial concentrations. That were used on endpoint PCR reactions In a second set of experiments, the modified adenosine analogues were added in a SYBR Green qPCR mix, and reactions performed using the same template and primers as above. The Ct (Threshold Cycle) parameter was measured for each condition. The Ct is the cycle number at which the fluorescence generated within a reaction crosses the fluorescence threshold. The higher the Ct, the lower the amount of product (or lower expression). Table 1 below presents the data from qPCR reactions.

TABLE 1 qPCR Results

| Gene | Sample | Ct Mean |
|---|---|---|
| 18SrRNA | Control-1 | 12.65 |
| 18SrRNA | Phosphate 0.3 mM (Final) | 15.98 |
| 18SrRNA | Phosphate 0.15 mM (Final) | 13.70 |
| 18SrRNA | Phosphate 0.075 mM (Final) | 12.78 |
| 18SrRNA | Control-2 | 12.34 |
| 18SrRNA | Hydroxy 0.3 mM (Final) | 14.84 |
| 18SrRNA | Hydroxy 0.15 mM (Final) | 13.43 |
| 18SrRNA | Hydroxy 0.075 mM (Final) | 12.88 |
| ACTB | Control-1 | 20.05 |
| ACTB | Phosphate 0.3 mM (Final) | 21.82 |
| ACTB | Phosphate 0.15 mM (Final) | 20.91 |
| ACTB | Phosphate 0.075 mM (Final) | 20.15 |
| ACTB | Control-2 | 20.07 |
| ACTB | Hydroxy 0.3 mM (Final) | 21.14 |
| ACTB | Hydroxy 0.15 mM (Final) | 20.55 |
| ACTB | Hydroxy 0.075 mM (Final) | 20.08 |

As can be seen from the data in Table 1, the addition of any of phosphate and hydroxyl substances led to decrease of the amplification of the template, and it is also important to note that the reaction was dose-dependent, meaning that more of any of phosphate and hydroxyl substances led to a higher Ct value. At the same concentration, the efficacy of inhibition of amplification was higher for phosphate than hydroxyl.

Influence on SARS-CoV2 RNA Polymerase

In addition to the above experiments, further assays testing the ability of the compounds according to the present invention to block the RNA polymerization function of SARS-COV-2 polymerase NSP12 we performed.

The tested compounds were adenosine analogues:

Compound A

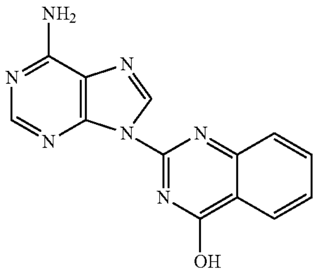

Compound B

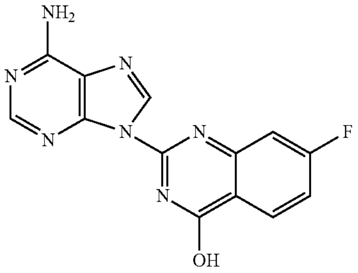

Compound C

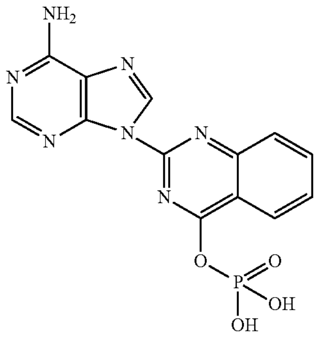

The RNA polymerase used in the assays consisted of the RdRp catalytic domain of RNA-directed RNA polymerase (Reference: PX-COV-P006, ProteoGenix), SARS-CoV-2 genomic RNA (2019 Novel Coronavirus; Strain: 2019-nCoV/USA-WA1/2020 (Reference: ATCC-VR-1986D, ATCC)), and the primers used in the assays consisted of (RNA or DNA) complementary to specific region, from Eurofins.

PCR reactions used the 10× First Strand Buffer and RNase Inhibitor from Amino Allyl MessageAmp™ II aRNA Amplification Kit (Reference: AM1753, Thermo), and dNTPs/rNTPs, respectively. Run conditions were 37° C. for 2 h and samples were run on agarose and PAGE gels.

A control reaction was carried out with a commercial polymerization inhibitor, Cordycepin 5'-triphosphate sodium salt (Reference: C9137, Sigma-Aldrich).

Figure 2:
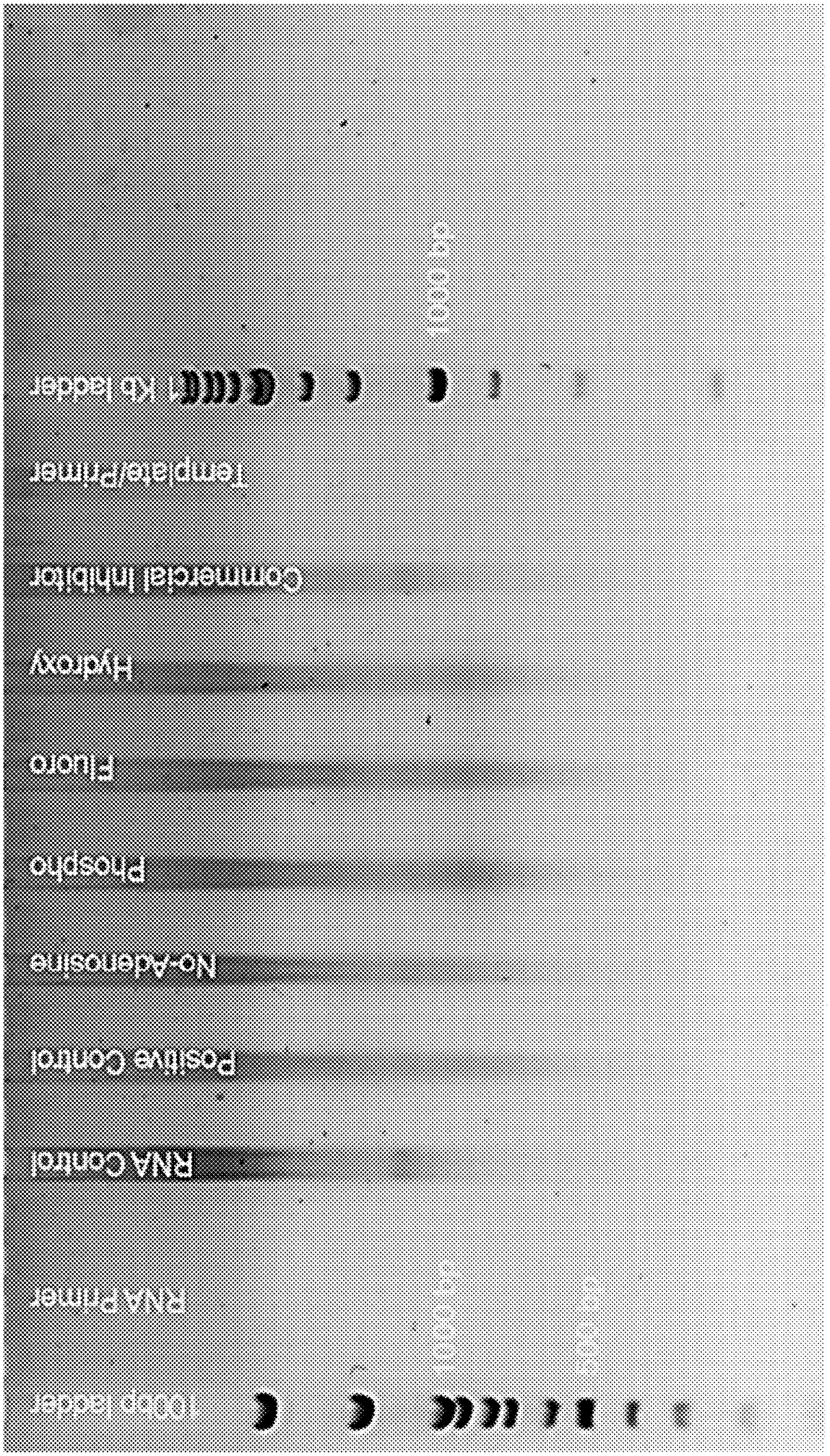
FIG. 2 depicts a PAGE gel stained with MidoriGreen Dye (stains both dsDNA, ssDNA, dsRNA and ssRNA) to show performance of different compounds and the control.

The performance of the different compounds and the control can be derived from FIG. 2, depicting a PAGE gel stained with MidoriGreen Dye (stains both dsDNA, ssDNA, dsRNA and ssRNA).

In FIG. 2, the lanes are labeled with, from left to right:

"100 bp Ladder"

This lane was loaded with a marker composition having marker fragments spaced by 100 bp to each other.

"RNA Primer"

This lane was loaded with specific RNA primers of approximately 24 bases, obtained from Eurofins Genomics.

"RNA Control"

This lane was loaded with genomic RNA from the 2019 Novel Coronavirus; Strain: 2019-nCoV/USA-WA1/2020 (Reference: ATCC-VR-1986D, ATCC)

"Positive Control"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs.

"No-Adenosine"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs, in equimolar amounts, except that no rATP was included.

"Phospho"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs in equimolar amounts, except that the standard amount for rATP was split 50:50 between rATP and Compound C.

"Fluoro"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs in equimolar amounts, except that the standard amount for rATP was split 50:50 between rATP and Compound B.

"Hydroxy"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs in equimolar amounts, except that the standard amount for rATP was split 50:50 between rATP and Compound A.

"Commercial Inhibitor"

This lane was loaded with the amplification product obtained from amplifying genomic RNA from the 2019 Novel Coronavirus; Strain: 2019-nCoV/USA-WA1/2020 (Reference: ATCC-VR-1986D, ATCC), using the NSP12/RdRp catalytic domain of RNA-directed RNA polymerase (Reference: PX-COV-P006, ProteoGenix) of SARS-CoV2 and the RNA primers (same as the lane "RNA Primer"), using the 10× First Strand Buffer and RNase Inhibitor from Amino Allyl MessageAmp™ II aRNA Amplification Kit (Reference: AM1753, Thermo), and rNTPs, in equimolar amounts, except that the standard amount for rATP was split 50:50 between rATP and the commercial inhibitor. The inhibitor is a modified nucleotide analogue, and lacks a 3'-hydroxyl group.

"Template/Primer"

This lane was loaded with a mix of RNA Control and Primer, without any other component, loaded on gel, to ensure that this mixture does not give any signal on the length of the substances.

"1 Kb Ladder"

This lane was loaded with a marker composition having marker fragments spaced by 1000 bp to each other.

Based on the above data, it is demonstrated that the addition of either of compounds A, B or C inhibits the in vitro replication of the SARS-CoV-2 RNA via the SARS-CoV-2 RNA polymerase, and the smears in the respective lanes indicate that the amplification products have varying sizes reflecting inhibition of the polymerization reaction at several stages. Note that in each case, the compounds A, B, C were in competition to dATP and rATP in an effort to emulate in vivo conditions. In addition, the smear is located below the material that is visualized in the lane "Positive control", which means that each compound was able to reduce the length of the amplification products and inhibit the polymerization activity of NSP12. The smears are located between 700-900 bp.

The RNA control has a smear above 3000 bp and a single band between 1000-1500 bp. On the positive control, the band is much fainter and a smear between 600-1200 bp is observed. This indicates polymerization on different fragments, which also explains the smear.

The non-adenosine lane shows an image similar to the RNA control, since no polymerization occurred when the NSP12 should have incorporated adenosine nucleotides.

On the commercial inhibitor, the profile is also similar to RNA control, since also the polymerization blocked.

The primers are not observed since they are smaller than the 100 bp of the ladder.

REFERENCES

1. Fehr A R, Perlman S. Coronaviruses: an overview of their replication and pathogenesis. Methods Mol Biol. 2015; 1282:1-23. doi:10.1007/978-1-4939-2438-7_1
2. Hoffmann M, Kleine-Weber H, Schroeder S, et al. SARS-CoV-2 Cell Entry Depends on ACE2 and TMPRSS2 and Is Blocked by a Clinically Proven Protease Inhibitor [published online ahead of print, 2020 Mar. 4]. Cell. 2020; 50092-8674(20)30229-4. doi:10.1016/j.cell.2020.02.052
3. Song Z, Xu Y, Bao L, et al. From SARS to MERS, Thrusting Coronaviruses into the Spotlight. Viruses. 2019; 11(1):59. Published 2019 Jan. 14. doi:10.3390/v11010059
4. Kirchdoerfer, R. N., Ward, A. B. Structure of the SARS-CoV nsp12 polymerase bound to nsp7 and nsp8 co-factors. Nat Commun 10, 2342 (2019). https://dio.org/10.1038/s41467-019-10280-3

LIST OF REFERENCE SIGNS none

The invention claimed is:

1. A compound which is 2-(6-amino-9H-purin-9-yl)quinazolin-4-ol.

2. A compound which is 2-(6-amino-9H-purin-9-yl)quinazolin-4-yl dihydrogen phosphate.

3. A method of treating a coronavirus infection in a patient, comprising: administering to the patient a pharmaceutical formulation comprising 2-(6-amino-9H-purin-9-yl) quinazolin-4-ol.

4. The method according to claim 3, wherein the coronavirus is either SARS-COV or SARS-COV-2 or MERS-COV.

5. A method of treating a coronavirus infection in a patient, comprising: administering to the patient a pharmaceutical formulation comprising 2-(6-amino-9H-purin-9-yl) quinazolin-4-yl dihydrogen phosphate.

6. The method according to claim 5, wherein the coronavirus is either SARS-COV or SARS-COV-2 or MERS-COV.

* * * * *